United States Patent [19]

Moore

[11] Patent Number: 4,944,939

[45] Date of Patent: Jul. 31, 1990

[54] SHAVING PREPARATION FOR TREATMENT AND PREVENTION OF PFB (INGROWN HAIRS)

[76] Inventor: Milton D. Moore, 2940 Holly Hall, Houston, Tex. 77054

[21] Appl. No.: 378,450

[22] Filed: Jul. 10, 1989

Related U.S. Application Data

[63] Continuation of Ser. No. 132,496, Dec. 14, 1987, abandoned, which is a continuation-in-part of Ser. No. 922,076, Oct. 20, 1986, abandoned, which is a continuation-in-part of Ser. No. 822,608, Jan. 27, 1986, abandoned.

[51] Int. Cl.$^5$ .............................................. A61K 7/15
[52] U.S. Cl. ...................................................... 424/73
[58] Field of Search ......................................... 424/73

[56] References Cited

PUBLICATIONS

Brauner et al., Cutis, vol. 23, Jan. 1979, pp. 61–66, "Pseudofolliculitis Barbae—Medical Consequences of Interracial Friction in the U.S. Army".
Alexander et al., "Pseudofollicalitis Barbae in the Military" Journal of the National Medical Association, vol. 66, No. 6, pp. 459–479.

*Primary Examiner*—Nathan M. Nutter
*Attorney, Agent, or Firm*—William E. Shull; Eric Mirabel

[57] ABSTRACT

Disclosed is a shaving preparation to aid in prevention and treatment of PFB (ingrown hairs), which includes from about 0.1 to 6% by weight salicylic acid; a glucocorticoid in amount effective to reduce inflammation; and from about 0.5 to 5% by weight sulfur. In the shaving preparation the glucocorticoid can be, for example, triamcinolone acetate (about 0.025 to 0.1% by weight) hydrocortisone USP (about 0.1 to 2.5% by weight), or hydrocortisone acetate USP (about 0.1 to 2.5% by weight), and the sulfur can be in precipitated, sublimed or colloidal form. A number of other ingredients can also be included. Alternatively, the preparation can be separated so the active ingredients are in two or three separate parts, which are applied at various stages in the shaving process. The preparation is to be applied to the skin surface before and/or after shaving.

7 Claims, 1 Drawing Sheet

SHAVING PREPARATION FOR TREATMENT AND PREVENTION OF PFB (INGROWN HAIRS)

This is a continuation of co-pending application Ser. No. 07/132,496 filed on Dec. 14, 1987 and now abandoned.

This is a continuation-in-part application of my application entitled "Shaving Preparation for Treatment and Prevention of Ingrown Hairs" filed on Oct. 20, 1986 and assigned Ser. No. 922,076, which was a continuation-in-part of my application entitled "A Medicated Shaving Cream and Method for Using Same," filed on Jan. 27, 1986 and assigned Ser. No. 822,608 and now abandoned. I hereby claim priority of the Jan. 27, 1986 filing date and also abandoned application Ser. No. 922,076.

FIELD OF THE INVENTION

The invention relates to a shaving preparation to aid in treatment and prevention of the skin condition pseudofolliculitis barbae ("PFB"), also known as ingrown hairs or razor bumps.

BACKGROUND OF THE INVENTION

In civilized nations, men have customarily attempted, and sometimes are required, to make it appear as if there were no hairs on their faces and throats. This is usually accomplished in a morning-time, often sleepy-eyed, ritual in which the unsightly stubble is shaved or removed. This ritual is not, however, without its casualties. It is to the unfortunate sufferers of PFB, the fallout from that ritual, that this invention is directed.

Shaving often induces the hairs acted upon to grow inwardly, causing the condition known as PFB or ingrown hairs. Inward growth results when hairs which are sharpened by shaving either penetrate the epidermis in an arc or pierce the follicular wall. This penetration elicits a foreign body reaction known as a papule. See G. J. Bruner et al., "Pseudofolliculitis Barbae Medical Consequences of Interracial Friction in the U.S. Army," 23 CUTIS 61 (1979). Ingrown hairs can also be the result of hairs which never exit from the skin, continue growing inwardly, and cause an inflammatory reaction known as pustules.

While PFB usually is not considered serious, it can cause multiple papules, disfiguring hyperpigmentation, and in severe cases, hypertrophic or keloidal scarring. Some PFB victims even find it painful to put their faces on pillows.

Most victims of PFB are black males. This is believed to be due to the natural curvature of the facial hair and hair follicules of black men. See A. M. Alexander & W. I. Delph, "Pseudofolliculitis in the Military," 66 *J. Nat'l Med. Soc'y* 459 (1974). Furthermore, the more severe cases of the condition are usually seen in blacks.

The only sure cure for PFB is to stop shaving. As the beard grows, intrinsic spring-like forces withdraw the hair shafts from their "false follicules" ("pseudo" of "pseudofolliculitis" meaning "false") and allow healing of the affected skin. When the victim ceases shaving and his beard begins to grow, however, he is likely to suffer the insidious consequences of PFB: discrimination and rejection by society, sometimes resulting in hindrance of employment and career. For example, black servicemen who do not shave are often discriminated against by their superiors. See A. M. Alexander & W. I. Delph, "Pseudofolliculitis in the Military," 66 *J. Nat'l Med. Soc'y* 459 (1974). There have also been some highly-publicized lawsuits which center on the discriminatory effect blacks suffer as a result of employers' no-beard policies.

Several methods for treating PFB have been proposed for those who choose to continue the hair removal ritual. One such method includes the use of depilatories (hair removers) rather than shaving. However, these often can cause raw and tender skin when used on the face. Furthermore, many depilatories have a highly objectionable odor akin to that of rotten eggs.

Another proposed treatment for PFB includes use of a foil-guarded razor. See A. M. Alexander, "Evaluation of a Foil-Guarded Shaver in the Management of Pseudofolliculitis Barbae," 27 CUTIS 534 (1981). This PFB razor has a serrated foil guard that purportedly cuts hair but does not shave so closely as to induce inward growth. One company is also believed to be manufacturing an electric razor for the treatment of PFB.

Another proposed solution includes treating the edge of a razor with a water-repellant compound after wetting the skin surface to be shaved. This measure attempts to reduce the inward pull on the hairs by reducing friction. See U.S. Pat. No. 4,178,364.

Until the advent of the present invention, however, no one has suggested treating the skin of the PFB victim to reduce the likelihood that shaving will induce inward hair growth. Nor has anyone suggested treating the skin of the PFB victim to help free trapped hairs and to lessen the irritation caused by such hairs.

SUMMARY OF THE INVENTION

The shaving preparation of the present invention includes salicylic acid, which causes thinning of the upper layer of the skin in order to help free ingrown hairs and also to reduce the likelihood that other hairs will be trapped by shaving, a glucocorticoid to counter inflammation, and sulfur to counter infection. The ranges of these ingredients are approximately as follows:

(1) Salicylic acid, from about 0.1 to 6% by weight;
(2) Sulfur, from about 0.5 to 5% by weight; and
(3) Glucocorticoid, a concentration sufficient to reduce inflammation.

If the glucocorticoid is triamcinolone acetonide, the concentration is from about 0.025 to 0.1% by weight. If using triamcinolone, the concentration is from about 0.02 to 0.1% by weight. If using hydrocortisone USP or hydrocortisone acetate USP, the concentration is from about 0.1 to 2.5%. For Dexamethasone USP, the concentration is about 0.04%. Any other glucocorticoid may also be used in the dosage range recommended for it for topical application.

The shaving preparation of the present invention will typically also include a carrier or vehicle to carry the active ingredients as well as other ingredients, for example, preservatives, emulsifiers, and menthol, which gives a cooling effect when applied to the skin.

The invention will now be discussed with reference to the drawings.

DESCRIPTION OF THE DRAWINGS

Skin 10 of FIGS. 1–7 has a follicle 12 and upper and lower layers 14 and 16 respectively. In FIG. 1, hair 18 is shown growing from follicule 12 through lower layer 16 (the dermis), layer 14 (the epidermis), to outside skin 10 and then back into layer 14, thereby forming a false ("pseudo") follicle. An inflamed condition, papule 20, results.

Figure 1:
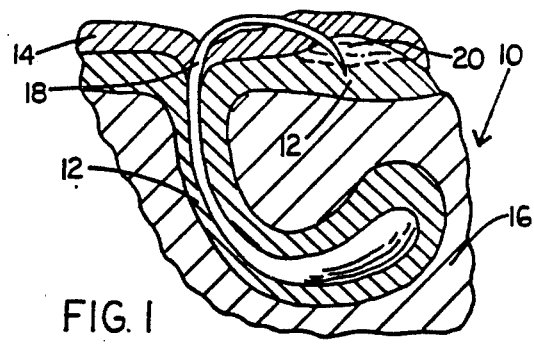
FIG. 1 shows a cross-sectional area of the skin with an ingrown hair forming a papule.
Figure 2:
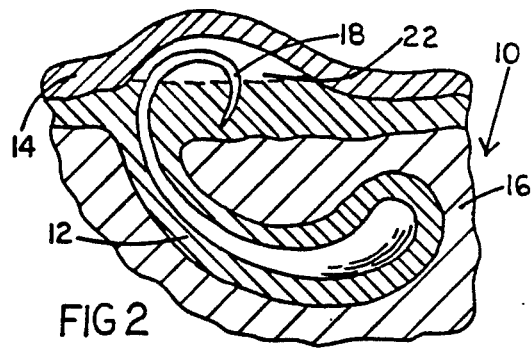
FIG. 2 shows a cross-sectional area of the skin with an ingrown hair forming a pustule.

Another type of inflamed condition, pustule 22, is depicted in FIG. 2. In that figure, hair 18 never exits the skin 10. Instead, it grows beneath the upper layer 14.

Figure 3:
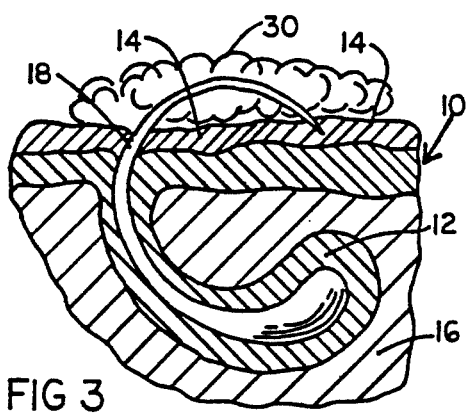
FIG. 3 shows the hair of FIG. 1 with a shaving preparation of the present invention applied thereto.
Figure 4:
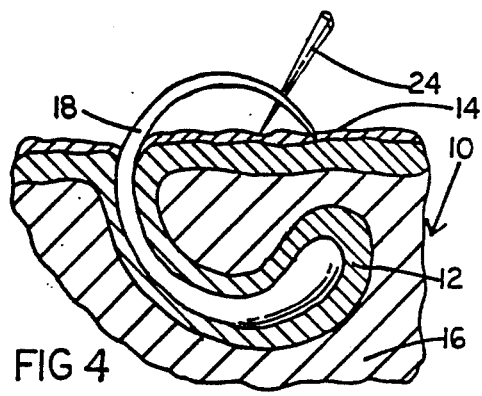
FIG. 4 shows the use of a tool to aid in freeing the hair of FIG. 1.
Figure 5:
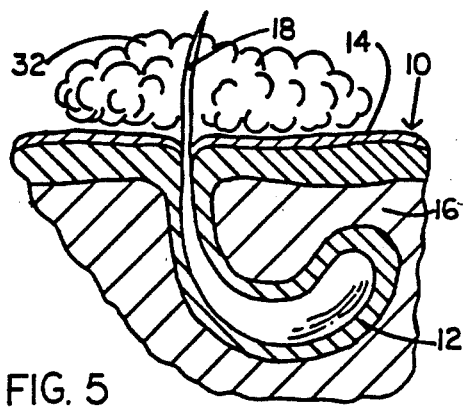
FIG. 5 shows a freed hair with a conventional shaving cream applied to the surrounding skin.
Figure 6:
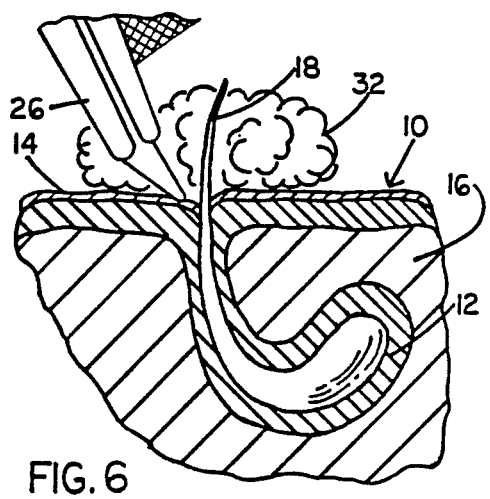
FIG. 6 shows a razor approaching the freed hair of FIG. 5.
Figure 7:
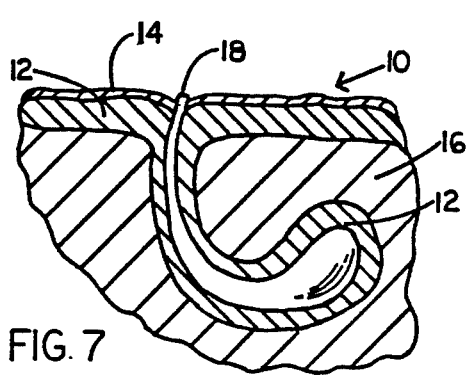
FIG. 7 shows the hair of FIG. 5 after it has been cut with the razor of FIG. 6.

In FIG. 3 a cream 30 containing, inter alia, salicylic acid is applied to skin 10. This results in a thinning of upper layer 14 as shown in FIG. 4, which makes it easier to free hair 18 with tool 24. FIGS. 5 & 6 show skin 10 following freeing of hair 18—note the thinned condition of upper layer 14—with a conventional shaving preparation 32 applied. In FIG. 6 razor 26 is approaching hair 18. FIG. 7 shows hair 18 after cutting.

The preferred embodiments of the invention will now be described.

DESCRIPTION OF THE PREFERRED EMBODIMENTS

The shaving preparation of the invention is made by combining the active ingredients (and any other desired ingredients) together with a suitable carrier, such as a lotion, an ointment base, or an emulsion base, in a manner well-known in the pharmaceutical arts. Any of these carriers can be made by well-known methods.

Where the active ingredients are to be administered in the form of a suspension/solution, i.e. in a lotion, one suitable lotion is white lotion NF, which has the following formula:

| Zinc Sulfate | 40.0 g |
|---|---|
| Sulfurated Potash | 40.0 g |
| Purified Water, a sufficient quantity to make | 1000.0 g |

White lotion NF is made by dissolving the zinc sulfate and sulfurated potash separately, each in 450 ml of purified water, and then filtering each solution. The sulfurated potash solution is then added slowly to the zinc sulfate solution with constant stirring. The remainder of the purified water is finally added, and the solution is mixed.

Exemplary shaving preparations where the base is white lotion NF are set forth below in Examples I and II. These suspension/solutions are made in a manner well known to those skilled in the art and in accordance with practice in standard reference texts, for example, Remington's Pharmaceutical Sciences 15th Ed.

EXAMPLE I

A shaving preparation of the invention includes the following ingredients: 0.5% by weight hydrocortisone acetate, 2% by weight salicylic acid, 2% by weight precipitated sulfur, 5% by weight propylene glycol (which acts as a wetting agent or emulsifier), 0.25% menthol, the remainder being white lotion NF. Mineral oil may be substituted for propylene glycol, and hydrocortisone USP may be substituted for hydrocortisone acetate.

The function of the various other ingredients is set forth above under "SUMMARY OF THE INVENTION."

EXAMPLE II

A shaving preparation of the invention has the following ingredients: 0.025% by weight triamicinolone acetonide, 3% by weight salicylic acid, 3% by weight precipitated sulfur, 8% by weight propylene glycol, 0.25% by weight menthol, the remainder being white lotion NF. Again, mineral oil may be substituted for propylene glycol.

As noted above, the active ingredients can also be applied using an ointment base or emulsion base as the vehicle. Examples of shaving preparations of the present invention where the vehicle is an ointment base or emulsion base are set forth below. These emulsion and ointment bases are made in a manner well known to those skilled in the art and in accordance with practice in standard reference texts, for example, Remington's Pharmaceutical Sciences 15th Ed.

EXAMPLE III

Hydrophillic Ointment USP is made as follows:

| Methylparaben | 0.25 g |
|---|---|
| Propylparaben | 0.15 g |
| Sodium Lauryl Sulfate | 10.0 g |
| Propylene Glycol | 250 g |
| Stearyl Alcohol | 250 g |
| White Petrolatum | 370 g |
| Purified Water, sufficient to make | 1000 g |

The stearyl alcohol and the white petrolatum are melted on a steam bath and warmed to about 75° C. The other ingredients, which have been previously dissolved in water, are then added and warmed to about 75° C. The mixture is stirred until it congeals.

To add the other ingredients needed for the shaving preparation, the Hydrophyllic Ointment USP is melted and mixed with colloidal sulfur, salicylic acid, triamcinolone, and menthol, so that the final product has 0.5 to 5% by weight colloidal sulfur, 0.1 to 6% by weight salicylic acid, 0.02 to 0.1% by weight triamcinolone, and 0.25% by weight menthol.

EXAMPLE IV

Cold Cream USP is made as follows:

| Spermaceti | 125 g |
|---|---|
| White Wax | 120 g |
| Mineral Oil | 560 g |
| Sodium Borate | 5 g |
| Purified Water | 190 ml |

The spermaceti and the white wax are reduced to small pieces, and melted on a steam bath with the mineral oil. The heat is continued until the temperature of the mixture reaches 70° C. The sodium borate is dissolved in the purified water and warmed to 70° C., and the warm solution is gradually added to the melted mixture with rapid and continuous stirring until it has congealed.

To add the other ingredients needed for the shaving preparation, the Cold Cream USP is first warmed slightly. Then, it is mixed with colloidal sulfur, salicylic acid, hydrocortisone which has been levigated with 10.0 g of mineral oil to make Hydrocortisone Cream USP, and menthol, so that the final product has 0.5 to 5% by weight colloidal sulfur, 0.1 to 6% by weight salicylic acid, 0.25 to 2.5% by weight hydrocortisone, and 0.25% by weight menthol.

EXAMPLE V

Rose Water Ointment NF is made as follows:

| | |
|---|---|
| Spermaceti | 125 g |
| White Wax | 120 g |
| Almond Oil | 560 g |
| Sodium Borate | 5 g |
| Stronger Rose Water | 25 ml |
| Purified Water | 165 ml |
| Rose Oil | 0.2 ml |

The spermaceti and the white wax are reduced to small pieces, the almond oil is added, and this composition is melted on a steam bath. The heat is continued until the temperature of the mixture reaches 70° C. The sodium borate is dissolved in the purified water and stronger rose water, and warmed to 70° C. The warm solution is gradually added to the melted mixture with rapid and continuous stirring until it has cooled to about 45° C. The rose oil is then incorporated.

To add the other ingredients needed for the shaving preparation, the Rose Water Ointment NF is first warmed slightly. Then, it is mixed with colloidal sulfur, salicylic acid, hydrocortisone which has been levigated with 10.0 g of mineral oil to make Hydrocortisone Cream USP, and menthol, so that the final product has 0.5 to 5% by weight colloidal sulfur, 0.1 to 6% by weight salicylic acid, 0.25 to 2.5% by weight hydrocortisone, and 0.25% by weight menthol.

EXAMPLE VI

Zopf Emollient Cream is made as follows:

| | |
|---|---|
| White Petrolatum | 41 g |
| Microcrystalline Wax | 3 g |
| Fluid Lanolin | 10 g |
| Sorbitan Monooleate | 4.75 g |
| Polysorbate 80 | 0.25 g |
| Purified Water | 41 g |

An aqueous dispersion of sorbitan monooleate and polysorbate 80 is warmed to 75° and added slowly to the melted wax, white petrolatum, and fluid lanolin phase. The mixture is stirred until congealed.

The active ingredients needed to make the shaving preparation are added as described above in Examples IV and V.

EXAMPLE VII

Phase A of Hoch Formula contains the following:

| Phase A of Hoch Formula contains the following | |
|---|---|
| Fluid Lanolin | 5 g |
| Castor Oil | 35 g |
| Sorbitan Monostearate | 2 g |
| Mineral Oil | 36.7 g |
| Stearic Acid | 4 g |
| Propylparaben | 0.2 g |
| Phase B of Hoch Formula contains the following | |
| Polyethylene 20 Sorbitan Monostearate | 1.0 g |

| -continued | |
|---|---|
| Triethanolamine | 0.9 g |
| Methylparaben | 0.2 g |
| Purified Water | 15 g |

Phase A is heated to 78° C. and phase B to 70° C., whereupon phase B is added to phase A and the mixture is stirred until it cools to 25° C.

The active ingredients needed to make the shaving preparation are added as described above in Examples IV and V.

EXAMPLE VIII

It is also possible to carry the glucocorticoid in a separate vehicle from that which carries the salicylic acid and the sulfur. In such a case, the salicylic acid and the sulfur could be carried in any of the vehicles of Examples I to VII, or any other suitable vehicle. The glucocorticoid could be, for example, Hydrocortisone USP, which is made by levigating the proper amount of hydrocortisone with 10.0 g of mineral oil.

It should be understood that in any of the Examples III to VIII above, other ingredients, such as preservatives, thickeners, gelling agents, solvents, emulifying agents and emollients, can also be added. Such other ingredients can include ethyl alcohol, sesame oil, propylene glycol, carbopol 940, carbomer 940, stearic acid, silicone, DL panthenol, triethanolamine, and butylated hydroxyanisole. Further, the glucocorticoid need not be the one specified but could be any one that either is or could be made compatible with the mixture. Also, the sulfur need not be in colloidal form but can be any compatible variety, for.. example, precipitated sulfur or sublimed sulfur. A great number of variations of the carriers for carrying the active ingredients are also possible. Accordingly, the suitable carriers are not limited to those specified above. Finally, although Example VIII only mentions separating the glucocorticoid from the other active ingredients, it is also within the scope of the invention to separate either of the other two active ingredients, i.e., sulfur and salicylic acid.

The shaving preparation of Examples I to VII is to be applied several hours before shaving. This early application allows the salicylic acid time to act to thin the skin surrounding the ingrown hairs. This thinning action reduces the likelihood that shaving will act to induce hairs to grow inwardly, while it aids in freeing any trapped hairs. Early application also allows the glucocorticoid time to act to reduce papule or pustule inflammation, and thus gives further aid in freeing trapped hairs. Thinning the skin and reducing inflammation surrounding ingrown hairs enables some of the ingrown ends of such hairs to spring free of the skin. Any hairs which do not spring free and remain trapped can be mechanically lifted immediately before shaving with a tool such as that described in my co-pending application Ser. No. 897,871 and illustrated generally in FIG. 4 of this application. Following shaving, a second treatment of the shaving preparation is applied to further reduce inflammation and promote healing.

In applying the shaving preparation of Example VIII, where the glucocorticoid (hydrocortisone USP) is separate from the other two active ingredients, the hydrocortisone USP is applied 8 to 12 hours before shaving. Any trapped hairs are then lifted with the tool illustrated generally in FIG. 4. Immediately before shaving, the beard is wetted with a solution of propylene glycol and water. A conventional shaving foam, soap, or other preparation can then be applied (e.g., RISE TM, EDGE TM, or the like).

After shaving, the vehicle with the salicylic acid and sulfur is applied. If ingrown hair problems are severe, the hydrocortisone USP can be applied after shaving as well. Application of either the hydrocortisone USP or the salicylic acid/ sulfur vehicle can be repeated as necessary.

It must be understood that the examples of the compositions of the present invention and their method(s) of use are exemplary only, and can be departed from without departing from the spirit of the invention. These examples are not to limit the scope of protection, which is defined in the claims which follow and includes all equivalents of the claimed subject matter.

I claim:

1. A shaving preparation to aid in prevention and treatment of pseudofolliculitis barbae or ingrown hairs, consisting essentially of:
    from about 0.1 to 6% by weight salicylic acid;
    a glucocorticoid in amount effective to reduce inflammation caused by ingrown hairs;
    from about 0.5 to 5% weight sulfur.

2. The shaving preparation of claim 1 wherein the glucocorticoid is triamcinolone acetate in amount from 0.025 to 0.1% by weight, hydrocortisone USP in amount from 0.1 to 2.5% by weight, or hydrocortisone acetate USP in amount from 0.1 to 2.5% by weight, and the sulfur is in precipitated, sublimed or colloidal form.

3. A method of treating and preventing pseudofolliculitis barbae or ingrown hairs comprising applying a shaving preparation consisting essentially of about 0.1 to 6% by weight salicylic acid, about 0.5 to 5% by weight sulfur, and a glucocorticoid in amount effective to reduce inflammation caused by ingrown hairs, to a skin area to be shaved prior to shaving.

4. The method of claim 3 further including applying said shaving preparation to said skin area after shaving.

5. The method of claim 4 further including applying additional hydrocortisone USP in amount sufficient to counter inflammation after shaving.

6. A method of treating and preventing pseudofolliculitis barbae or ingrown hairs resulting from shaving comprising:
    applying hydrocortisone USP 0.5% in amount sufficient to counter inflammation several hours prior to shaving;
    mechanically lifting any ingrown hairs;
    applying a solution of propylene glycol and water to a skin area to be shaved, the proportion of propylene glycol in said solution being sufficient to wet the hairs;
    shaving said skin area;
    applying a shaving preparation comprising 0.5 to 5% sulfur and 0.1 to 6% salicylic acid to said skin area.

7. The method of claim 6 further including again applying said shaving preparation and again applying hydrocortisone USP 0.5% following shaving.

* * * * *